United States Patent [19]

Hirschfeld

[11] 4,447,546

[45] May 8, 1984

[54] FLUORESCENT IMMUNOASSAY EMPLOYING OPTICAL FIBER IN CAPILLARY TUBE

[75] Inventor: Tomas E. Hirschfeld, Livermore, Calif.

[73] Assignee: Myron J. Block, North Salem, N.H.

[21] Appl. No.: 410,340

[22] Filed: Aug. 23, 1982

[51] Int. Cl.$^3$ .................. G01N 21/00; G01N 21/64; G01N 33/54; G01N 33/58

[52] U.S. Cl. .................................. 436/527; 250/227; 250/365; 356/445; 422/57; 436/805; 436/807

[58] Field of Search ............... 436/527, 805, 807; 422/56, 57; 250/227, 365; 356/445

[56] References Cited

U.S. PATENT DOCUMENTS

| | | | |
|---|---|---|---|
| 3,604,927 | 9/1971 | Hirschfeld | 356/311 X |
| 3,939,350 | 2/1976 | Kronick | 250/302 X |
| 3,998,591 | 12/1976 | Eckfeldt | 422/86 X |
| 4,050,895 | 9/1977 | Hardy | 436/805 X |
| 4,106,909 | 8/1978 | David | 436/100 X |
| 4,133,639 | 1/1979 | Harte | 422/57 X |
| 4,321,057 | 3/1982 | Buckles | 422/58 X |
| 4,368,047 | 1/1983 | Andrade | 436/805 X |

FOREIGN PATENT DOCUMENTS 75353 3/1983 European Pat. Off. .

*Primary Examiner*—Sidney Marantz
*Attorney, Agent, or Firm*—Schiller & Pandiscio

[57] ABSTRACT

Fluorescent immunoassay apparatus and method employing a disposable consisting, in a preferred embodiment, of a short length of precise diameter capillary tubing having an axially disposed optical fiber to which is immobilized a monolayer of a component of the antibody-antigen complex (e.g., an antibody), an inert diluent, and a preload of a known amount of tagged complement to the immobilized component (e.g., a fluorescent-tagged antigen). The dimensions of the fiber and the capillary tubing are chosen so as to allow the tube to fill itself by capillary action once an end of the tube is immersed into the sample. Precise timing and ballistic measurements may, if desired, be avoided by insuring the incubation time is larger than the diffusion time necessary to scavenge the volume between the fiber and the capillary tubing. Fluorimetric measurement is made by total reflection fluorescence techniques.

15 Claims, 4 Drawing Figures

FLUORESCENT IMMUNOASSAY EMPLOYING OPTICAL FIBER IN CAPILLARY TUBE

BACKGROUND OF THE INVENTION

This invention relates to immunoassays, and more particularly to such assays wherein a fluorescent tag capable of emitting fluorescent radiation when excited by more energetic exciting radiation is incorporated into a constituent of an antigen-antibody or similar complex.

Immunoassays, in which aliquots of sample and one or more reagents are variously reacted to form antigen-antibody or similar complexes which may then be observed in order to assay the sample for the presence and titer of a predetermined moiety of the complex, are well known. Typical of such assays are those wherein a specific antibody is used to measure the quantity of the antigen for which it is specific (or vice versa). However, the technique has been extended to quantitate haptens (including hormones, alkaloids, steroids, and the like) as well as antigens, and antibody fragments (i.e., Fab) as well as complete antibodies, and it is in this broader sense that the present invention should be understood.

As is well known, sensitive immunoassays employ tracer techniques wherein a tagged constituent of the complex is incorporated into the reagent, the non-complexed tagged reagent being separated from the complexed reagent, and the complex (or non-complexed reagent) then quantitated by observing the tag. Both radioisotopes and fluorescent markers have been used to tag constituents of immunoassay reagents, the tag being respectively observed by a gamma ray counter or a fluorometer. The present invention is, however, directed only to those assay which rely on fluorescence.

The separation of the non-complexed tagged moiety from the complexed is commonly accomplished by immobilizing a predetermined one of the components of the complex to a solid phase (such as the inside wall of a test tube, glass or polymeric beads, or the like) in such a way as not to hinder the component's reactivity in forming the complex. As an example, an antibody such as immunoglobulin G (IgG) may be bound by its carboxyl terminations to a solid phase, such as glass, by a silyl compound such as 3-aminopropyltrimethoxysilane, thereby leaving the antibody's antigen reactive amino terminations free. Any complex formed incorporating the immobilized component may then be physically separated from the non-reacted complement remaining in solution, as by aspirating or decanting the fluid from a tube or eluting the fluid through a particulate bed.

In competition immunoassay, the reagent consists of a known quantity of tagged complement (such as antigen) to the immobilized component of the complex (in this instance, antibody). The reagent is mixed with a fixed quantity of the sample containing the untagged complement to be quantitated. Both tagged and untagged complement attach to the immobilized component of the complex in proportion to their relative concentrations. After incubation for a set time, the fluid sample and reagent are separated. The complex immobilized to the solid phase is then illuminated with radiation of a wavelength chosen to excite fluorescense of the tag, and the fluorescense is measured. The intensity of the fluorescense of the immobilized complex is inversely proportional to the concentration of the untagged complement being assayed.

Alternatively, an assay may be made by immobilizing a quantity of an analog of the moiety to be quantitated (i.e., a substance which is immunologically similarly reactive) and reacting the sample with a known quantity of tagged complement. The tagged complement complexes with both the unknown quantity of the moiety in the sample and the immobilized analog. Again, the intensity of fluorescence of the immobilized complex is inversely proportional to the concentration of the (free) moiety being quantitated.

So-called "sandwich" immunoassays may be performed for multivalent complements to the immobilized component, the attached complement being then further reacted with a tagged analog of the imobilized component. Thus, bivalent antigen may be bound to an immobilized antibody and then reacted with a fluorescent tagged antibody, forming an antibody—antigen—tagged antibody sandwich that may then be separated from the unreacted tagged antibody. The intensity of the fluorescence of the thus formed immobilized complex is directly proportional to the concentration of the species being quantitated.

In any of the assays, accuracy in quantitation is determined in part by the technique of the laboratory personnel performing the assay. Thus, precision fluorescence immunoassay requires fluorometric measurement of a predetermined volume of the sample to which a predetermined quantity of reagent has been added at a known dilution. To insure that the necessary volume measurements are not the accuracy limiting step of the assay requires that the assay be performed by skilled personnel and often with precision apparatus, or alternatively, precisely constructed and preloaded disposable reagent kits (to insure the titer of reagent) together with an accurately timed diffusion process (to insure the size of the sample volume assayed.

It will be appreciated that the use of skilled personnel, precision apparatus, and accurate manipulative or timing requirements impact both the cost and wide-scale availability of an assay.

OBJECTS OF THE INVENTION

Accordingly, it is an object of the present invention to provide apparatus and methods for fluorescent immunoassay in which volume measurement is neither the accuracy limiting nor the labor skill determining step of the assay, thereby making precision immunoassay widely and inexpensively available.

It is a further object of the present invention to provide apparatus and methods for fluorescent immunoassay which do not require expensive precision manufacture nor accurate preloading of apparatus, reagent, or disposable.

Yet another object of the present invention is to provide a simple and accurate immunoassay wherein a low cost easily manipulated disposable insures the sample volume and supplies the proper quantity and dilution of reagent.

BRIEF DESCRIPTION OF THE INVENTION

These and other objects are accomplished in the present invention of an immunoassay apparatus and method in which a disposable consisting, in a preferred embodiment, of a length of precise diameter capillary tubing having an approximately axially disposed optical fiber to which is immobilized a monolayer of a component of the antibody-antigen complex (e.g., an antibody), an inert diluent, and a preload of a known amount of tagged complement to the immobilized component (e.g., a fluorescent-tagged antigen). The active length of the fiber is controlled by silicone coating all but a portion of the fiber, thereby making all but the uncoated portion chemically inert, prior to loading the fiber with the immobilized component, diluent, and tagged component. The immobilized component, the diluent, and the tagged component are made to have fixed composition and quantity by loading the active region of the fiber from a solution having appropriate concentrations of the reagents.

The dimensions of the fiber and the capillary tubing are chosen so as to allow the tube to fill itself by capillary action once an end of the tube is immersed into the sample. For a given size tube and fiber, a fixed volume of sample will be drawn into the tubing whenever it is dipped into sample and allowed to fill completely. However, it is sufficient to have the sample cover only the active length of the fiber (i.e., the portion of the fiber loaded with the immobilized component, tagged component, and diluent). This can be verified by observing the level of the sample in the capillary tubing relative to the inactivating silicone coating on the fiber. It is therefore not necessary to control precisely the capillary tubing's length or to insure its complete filling. The fluorometric measurement is made by total reflection fluorescence techniques.

The actual sampled volume is the product of the active fiber surface area multiplied by the distance from the fiber that can be sampled via diffusion processes. The large length-to-diameter ratio of the fiber insures that the length of the sampled region is very little longer than the fiber's active length. The depth of the layer sampled by diffusion depends on the incubation time. To avoid precise timing requirements, or to avoid ballistic measurements, it is only necessary to insure the incubation time is larger than the diffusion time necessary to scavenge the volume between the fiber and the capillary tubing. Thus, the volume sampled is easily controlled in the construction of the disposable of the present invention.

Since the assay kit of the present invention contains the necessary reagent in the required quantity and dilution, and since its construction controls the volume sampled, little training or skill is required of the technician performing the assay, nor is any precision volumetric, differential sensing, or timing apparatus required.

Inasmuch as fibers and capillary tubing of precise diameter and bore are readily and inexpensively available, and since the coating and loading of the fiber may be easily controlled during manufacture, it will be appreciated that the disposable of the present invention may be fabricated reasonably inexpensively.

Other objects of the invention will in part be obvious and will in part appear hereinafter. The invention accordingly comprises the apparatus possessing the construction, combination of elements, and arrangement of parts and the method comprising the several steps and the relation of one or more of such steps with respect to each of the others which are exemplified in the following detailed disclosure and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

In the figures, like index numbers refer to like elements.

Figure 1:
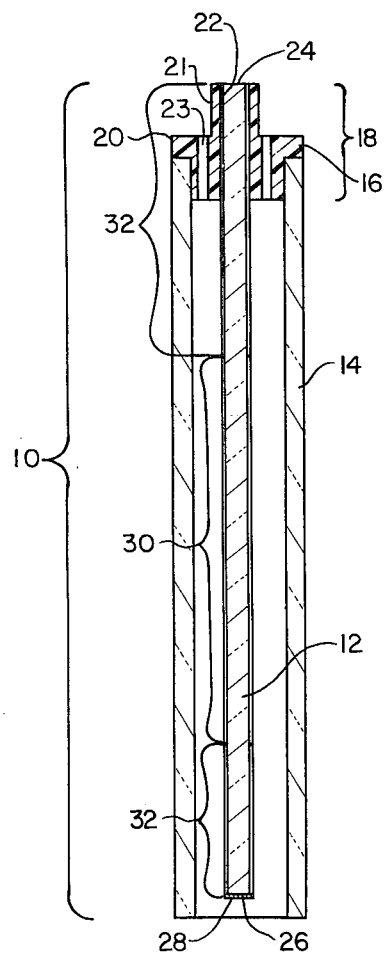
FIG. 1 is a longitudinal cross-sectional view of a disposable immunoassay kit which forms a preferred embodiment of the apparatus of the present invention.

With reference to terminology, it will be noted in the detailed description of the apparatus of this invention that portions of the apparatus are referred to as "upper" and "lower" portions. This is done wholly for convenience and to relate the description to the diagrammatic representations in the drawings. It will be appreciated that the apparatus can function in any position or orientation and it is within the scope of this invention to have it do so.

It is further to be understood that the representation in the figures is diagrammatic and no attempt has been made to indicate actual scales or ratios.

DETAILED DESCRIPTION

The present invention operates by total reflection fluorescence, coupled with tunneling of the fluorescent radiation, as described in copending application Ser. No. 406,324, filed Aug. 9, 1982, and assigned to the assignee of the present application, and to which reference may be had for further details of the optical mode of operation of the apparatus.

Referring to FIG. 1, there may be seen a longitudinal cross-sectional view of an immunoassay kit 10 made in accordance with the principles of the present invention. Kit 10 comprises optical fiber 12, capillary tube 14, and stopper 16.

Fiber 12 is an elongate substantially cylindrical optically transparent body adapted to propagate along its length through multiple total internal reflections optical radiation entering an end of the fiber within an established solid angle substantially rotationally symmetric about the fiber's axis. As is well known in the art of fiber optics, the maximum acceptance angle, with regard to the fiber axis, B, for the radiation entering the fiber and so propagated within it, is established by the refractive indices of the fiber and the surrounding medium. For radiation initially propagating through a medium of refractive index $n_o$, incident upon a fiber of refractive index $n_1$ otherwise surrounded by a material of refractive index $n_2$, the maximum acceptance angle may be found from the equation $$N.A. = n_o \sin B = (n_1^2 - n_2^2)^{\frac{1}{2}}, \qquad 1)$$

where N.A. is the so-called numerical aperture of the fiber. By way of example, but not limitation, fiber 12 may be any of a number of optically transparent materials, such as glass, quartz, polypropylene, polyolefin, nylon, or the like, chosen to have an index of refraction greater than that of the fluid sample being assayed (typically, an aqueous solution having an index of refraction near 1.33 or a serum sample having an index of refraction near 1.35) and further chosen to be relatively insoluble and non-reactive with the fluid. While other fiber diameters may be used, it has been found that 200 microns is satisfactory. For most assays, a fiber 25 mm in length appears adequate; however, it will be understood that the length of the fiber can be accommodated to the assay to be undertaken.

As will be described in detail hereinafter, fiber 12 is provided with a surface coating including means for attaching selected moieties of an antigen-antibody complex (as herein used, "antigen-antibody complex" includes complexes not only of complete antibodies and antigens, but complexes incorporating the immunologically reactive fragments of either or both).

Capillary tube 14 is preferably an optically transparent tube, its material of construction also being chosen to be relatively insoluble and non-reactive with the fluid being assayed. Thus, capillary tube 14 is preferably fabricated from such materials as glass, quartz, polypropylene, polyolefin, or the like. In a preferred embodiment, capillary tube 14 is of right circular cylindrical bore, having an inside diameter a few hundred microns larger than the diameter of fiber 12 (e.g., for a fiber diameter of 200 microns, capillary tube 14 may have an inside diameter of about 800 microns).

Stopper 16 is configured and dimensioned to fit within an end of capillary tube 14 and support an end portion 18 of fiber 12 substantially coaxially within the capillary tube. Additionally, stopper 16 provides a hard locating surface for positioning kit 10 in a fluorometer, as will be described hereinafter. To these ends, stopper 16 is preferably provided with a flange 20 having an overall diameter on the order of the outside diameter of capillary tube 14 and a centrally disposed ferrule-like extension 21 coaxial with a central bore 22. Bore 22 penetrates throughout stopper 16, and is dimensioned to secure end portion 18 of fiber 12. In a preferred embodiment, stopper 16 is molded in place about fiber 12, the stopper being preferably fabricated of a low index material, such as siloxane. Stopper 16 is further provided with one or more through perforations 23 communicating with the interior of capillary tube 14.

Fiber 12 passes through and is supported by stopper 16 so as to expose substantially all of the fiber but end portion 18 to the interior of capillary tube 14, leaving end face 24 of end portion 18 unobscured and conterminous with the extremity of bore 22 external to the capillary tube. End face 24 is preferably planar and disposed normal to the axis of fiber 12. Preferably, end face 24 is also highly transparent and free of blemishes which would tend to scatter light incident upon the end face. To this end, end face 24 may be optically polished, although it has been found that a fused quartz fiber may be cleaved to provide an adequate optical surface. Optionally, the end face 26 of the fiber distal from end face 24 is also polished flat or cleaved and further provided with a mirror coating 28 (or a separate mirror) disposed substantially normal to the fiber axis, thereby causing radiation trapped in the fiber to double pass the fiber. The overal dimensions of fiber 12, capillary tube 14, and stopper 16 are chosen to insure lower end face 26 of the fiber is within the capillary tube.

Prior to being assembled into kit 10, fiber 12 is provided a coating, as will be described, activating a region 30 of its cylindrical surface for the assay to be performed. In a preferred embodiment, the activated region 30 is restricted to a predetermined length of fiber 12 by a chemically and optically inert coating 32 of, for instance, low optical index silicone, extending over both ends of the fiber. It will be understood, however, that the dimensions of activated region 30 may be controlled by other means (e.g., by masking the fiber during coating), or, alternatively, the entire length of fiber 12 might be activated and the length of the fiber disposed within capillary tube 14 carefully controlled.

Figure 3:
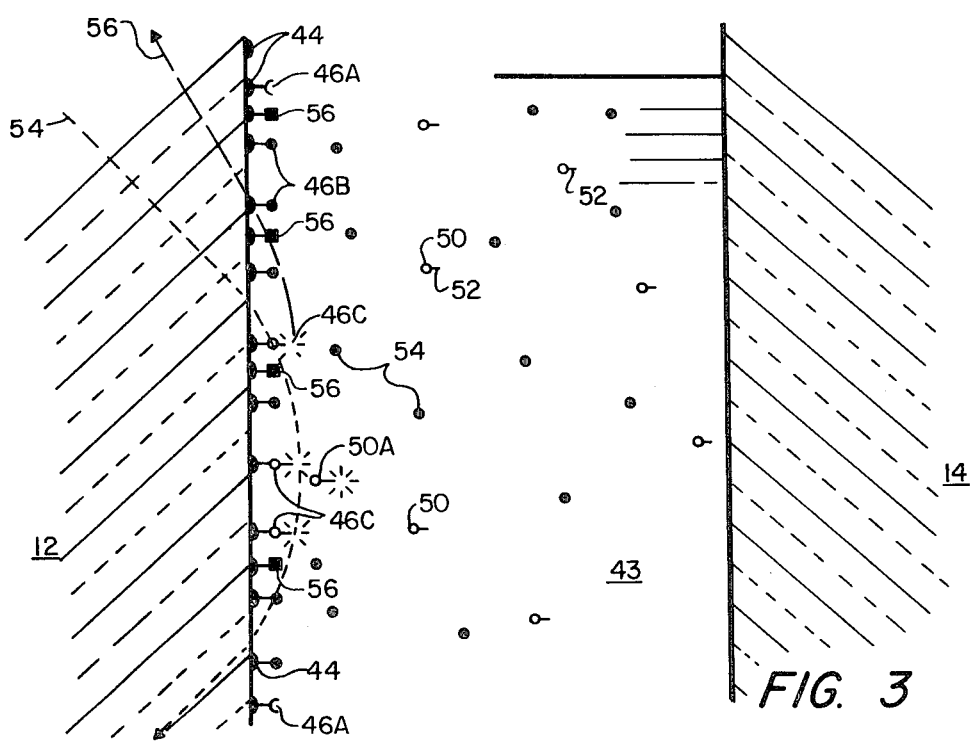
FIG. 3 is a stylized view of a portion of the kit of FIG. 1 (or 2), illustrating a typical immuno-chemical reaction in the realization of the invention.

Turning now to FIG. 3, there may be seen a highly stylized representation of a longitudinal cross-sectional portion of kit 10 within activated region 30 of fiber 12, filled with a sample 43 to be assayed.

The surface of fiber 12 within region 30 is provided with a plurality of coupling sites 44, to a number of which are bound a moiety 46 of the antibody-antigen complex. (As used herein, the phrase "moiety of an antibody-antigen complex" refers to immunologically reactive portion of such a complex, and includes haptens as well as complete antigens and antigen reactive antibody fragments as well as complete antibodies). Coupling sites 44 are so selected as to immobilize moieties 46 without appreciably affecting the reactivity (e.g., the affinity and avidity) of the moiety for the complementary portion of the complex. In a preferred embodiment, fiber 12 is of glass or quartz, coupling sites 44 are the reactive groups of a silyl compound such as 3-amino-propyltrimethoxysilane, and moieties 46 are an antibody such as immunoglobulin G (IgG). As noted hereinabove, for this particular combination of solid phase, coupling site 44 and moiety 46 may be bound through the antibody's carboxyl terminations, thereby leaving the antibody's antigen reactive amino terminations free. The method for preparing the glass surface of fiber 12, of attaching the silyl compound thereto, and of covalently bonding an antibody to the glass through the silyl coupling, are described by Weetall (U.S. Pat. No. 3,652,761), where may also be found a description of other silyl compounds and the methods by which carboxyl, amino, and other reactive groups of antibody or antigen (or their fragments) may be covalently bound to various inorganic materials. It should be noted that an extensive art for immobilizing antigens or antibodies to polymers also exists, and those skilled in the art will understand that coupling sites 44 for antigen or antibody might be provided on polymeric fibers also. Thus, for instance, if fiber 12 is of nylon (polyamide), the coupling may be in the form of the substitution of an appropriate radical for the hydrogen bound to the polymer's functional groups.

It should be noted that coupling sites 44 may also incorporate spacer groups, as are well known in the art, to insure sufficient separation between fiber 12 and moieties 46 as to minimize steric hindrance of the antibody-antigen binding process. For example, coupling sites 44 might include a polyethylene chain, as for example in the case of 1,6 diaminohexane or 6 aminohexanoic acid bound to fiber 12 through a peptide bond and respectively providing a free primary amino and a free carboxyl group for covalently binding to the carboxyl or amino termination of a protein moiety 46. Either of these coupling materials provide a 6-carbon chain between terminations, thereby spacing moiety 46 from fiber 12 by the corresponding distance. Similar appropriate coupling and spacer materials are well known in the arts of both immunoassay and affinity chromatography.

In a preferred embodiment, fiber 12 is provided with moiety 46 having occupied binding sites, as indicated at index numerals 46C, the moieties being in part provided with attached tagged complement 50 for competitive immunoassays. Thus, in one embodiment moiety 46 is an antibody, and a preloading of tagged antigen or hapten is incorporated into the coating of fiber 12. Each of the tagged components 50 is provided with a predetermined quantity of fluorophor 52, thereby providing a tag. The particular fluroescing compounds of interest for tagging include fluoresceine, tetramethylrhodamine, rare earth chelates, and the like. Methods for linking fluroescent tags to proteins are well known in the art, and many of the commercially available fluorescing compounds have groups for linking to proteins. Preferably, for competition assay, a fixed portion of coupling sites 44 are provided with a immunologically inert protein 56, such as albumin.

The coating can be made to have a fixed surface composition by using adsorption phenomena, as follows. For a coating solution prepared with appropriate concentration of the reagents, mere immersion of a fiber activated with the proper surface binding groups 44 will produce a surface monolayer of chemically bound protein. The proportion of, say, immunoglobulin to inert protein in this layer will be given by (but not identical to) their proportion in the solution. Any partial filling of the immunoglobulin active sites with tagged antigen will of course be maintained at the level in the solution.

After dipping, the fiber is removed from the coating solution. To prevent the adhering liquid layer from entraining additional reagent, the fiber is then quickly washed before further evaporation can occur. The protein layer, being covalently bound, will not be dislodged by this process. In order to prevent binding of more than one layer of protein, the bifunctional reagent must not alter the net charge of the protein (this can be controlled by adjusting the pH of the coating solution) and not have too long a spacer arm.

Figure 4:
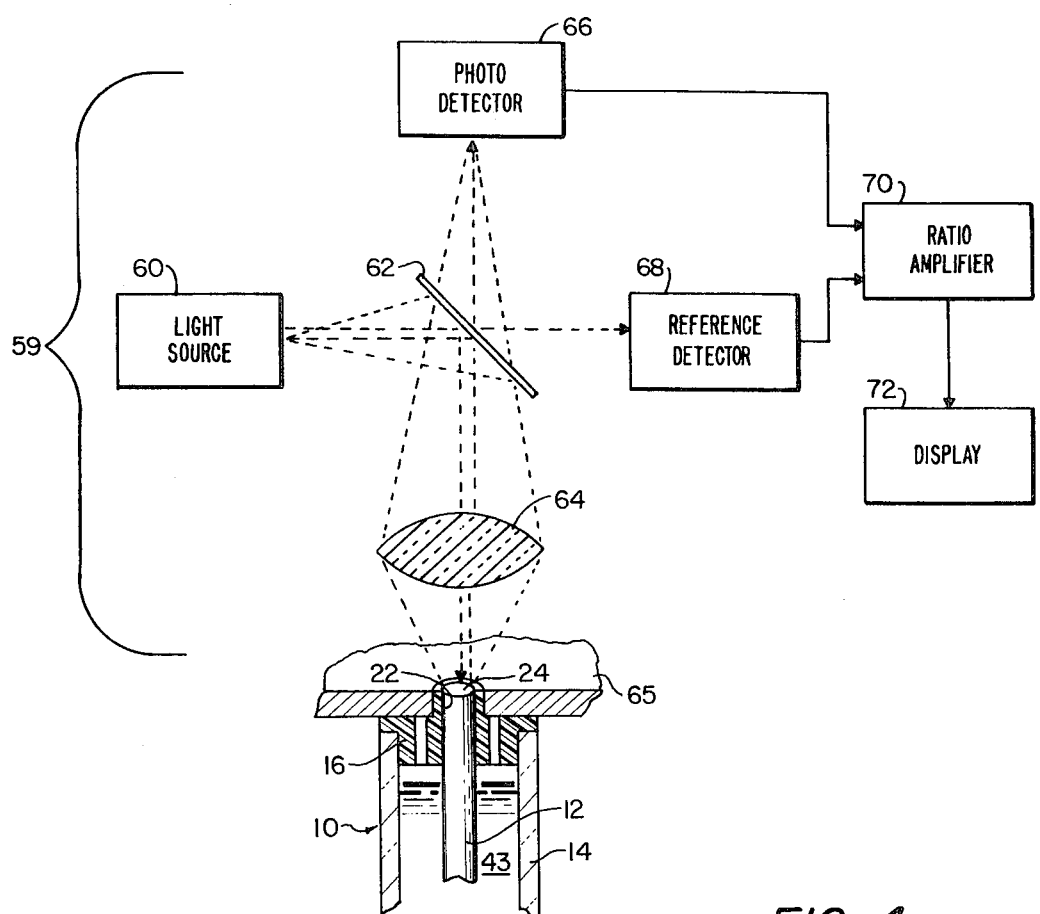
FIG. 4 is a schematic view of an exemplary fluorometer for use with the immunoassay kit of the present invention.

Kit 10 is intended for use with fluorometer 59 (FIG. 4). Fluorometer 59 comprises light source 60, dichroic beam splitter 62, objective 64, photodetector 66, reference detector 68, ratio amplifier 70, and display 72.

Light source 60 provides optical radiation of the appropriate frequency, chosen on the basis of the fluorophor used as the tag in the assay of interest, to excite fluoresense in the tagged component of the reagent. Light source 60 preferably provides this radiation over only a narrow wavelength band, chosen to maximize the fluorescence. Hence, light source 60 typically includes, in addition to the preferred tungstenhalogen lamp and associated power supply, a band-pass filter. Alternatively, it will be understood light source 60 might incorporate other sources, such as a mercury lamp, flash lamp, or a laser. Light source 60 also includes an appropriate beam shaping aperture and optics, as will be understood by those skilled in the art, to illuminate objective 64 with a beam of the appropriate vergence so as to permit the objective to image the source aperture on end face 24 of fiber 12 with no ray incident on the end face at an angle of incidence greater than that corresponding to the numerical aperture of the fiber.

Interposed between light source 60 and objective 64 is dichroic beamsplitter 62. In the preferred embodiment, beamsplitter 62 is a low-pass interference filter with a cut-off frequency chosen to be between the frequencies of maximum absorption and maximum fluorescence emission of the fluorophore of interest. Beamsplitter 62 thus reflects the high frequency (short wavelength) fluorescence exciting radiation from light source 60 and transmits the low frequency radiation corresponding to the fluorescence maximum of the fluorophor.

Objective 64 is selected to image light source 60 on end face 24 of fiber 12, so as to just fill the end face with an image of the beam shaping aperture of the source, the maximum angle of incidence of a ray being selected to be less than that corresponding to the numerical aperture of the fiber. Objective 64 is also selected so as to collect substantially all of the radiation exiting end face 24 over the numerical aperture of the fiber and image the end face at photodetector 66. As an aid in establishing the proper position of fiber 12, fluorometer 59 is preferably provided with a positioning means, such as aperture plate 65, dimensioned to accept ferrule-like extension 22 of stopper 16 and disposed to position end face 24 appropriately relative to objective 64.

Photodetector 66 is positioned to receive, through beamsplitter 62, an image of end face 24 of fiber 12 projected toward the photodetector by objective 64. Photodetector 66 preferably includes a photomultiplier (provided with appropriate power supply and field optics to restrict the detector's field of view to end face 24, as is well known in the art), chosen to have maximum sensitivity in the region of peak fluorescence of the fluorophor. Photodetector 66 is further preferably provided with a blocking filter corresponding to the band-pass filter provided light source 60.

Reference detector 68, preferably a photodiode, is disposed to intercept radiation from light source 60 passing through dichroic beamsplitter 62. Reference detector 68 is chosen for peak sensitivity in the spectral region of light source 60 passed by dichroic beamsplitter 62, and includes appropriate field stops and optics to limit its field of view to the source.

Ratio amplifier 70 is any of a number of well-known electronic means providing an output signal which is proportional to the ratio of a pair of input signals, so connected to the outputs of photodetector 66 and reference detector 68 as to provide a signal proportional to the ratio of the output of the photodetector to the reference detector. For instance, ratio amplifier 70 may be a variable gain amplifier amplifying the output from photodetector 66 and having a gain inversely proportional to the output from reference detector 68.

The output of ratio amplifier 70 is connected to and serves as the input for display 72. Display 72 is any of a number of devices that provides a visual signal proportional to an electrical input, and may be, for instance, a meter, a digital display, a strip chart recorder, or the like.

In operation, kit 10 is dipped into a sample to be assayed. Perforations 23 allow capillary tube 14 to fill itself by capillary action once its end is immersed in sample (for the proposed tube diameter, it will be advantageous to hold the fiber at a slant for filling).

A fixed volume of sample will thus be drawn into capillary tube 14 whenever it is dipped in the solution and allowed to fill completely. Actually, this precaution is not really needed, and it is sufficient to have the liquid only cover the entire active region 30 of fiber 12. This can be verified by observing the sample to cover the upper inactivating coating 32 on the fiber. It is therefore not necessary to control precisely the capillary's length or its complete filling.

The actual sampled volume will be given by the product of the surface area of active region 30 multiplied by the distance away from fiber 12 that can be sampled via the diffusion process. This distance depends upon the particulate size of the species of interest, the temperature, and the viscosity of the sample fluid. For typical values of these parameters, several hundred microns of serum may be substantially scavenged of antigen in incubation times on the order of 15 minutes. For such incubation times, the volume sampled is substantially the volume contained between fiber 12 and capillary tube 14 over the length of active region 30. The large length to diameter ratio available on the fiber insures that, for reasonably long incubation times, the length of the sampled region may be kept very nearly the length of region 30.

It should be noted that in competitive assays the ratio after equilibration between untagged antigen being quantitated and the tagged antigen of the reagent is the measurand. For an initially saturated monolayer of antibody and tagged antigen, the amount of untagged antigen that must be scavenged from the sample to occupy half the coupling sites 44 would require, at realistic titers of antigen in biological fluids, diffusion paths of several millimeters. Such long diffusion paths would clearly require excessive incubation times. It is for the purpose of balancing the ratio of tagged antigen to sampled antigen in a competitive assay that biologically inert protein 56, in fixed ratio to the antibody, is incorporated. The optimal ratio of inert protein to antibody will depend on the particular assay and the allowable incubation time. For normal levels of antigen and incubation times on the order of 15 minutes, a 100:1 ratio of inert protein to antibody appears satisfactory.

While the present invention may be used in a ballistic mode (i.e., by observing the rate of fluoescence increase), a preferred method is to make the incubation time long enough that the layer thickness completely sampled by diffusion is greater than the difference in diameters of tube 14 and fiber 12 (diameters are used for this difference since the fiber may not be centered). As noted previously, for such an incubation time, the entire cross section of the tube will be sampled over the length of active region 30. As the dimensions of fiber 12, capillary tube 14, and active region 30 are easily controlled during manufacture, the volume sampled can be made independent of the skill of the technician performing the assay. Such a method has the further advantage over the ballistic method in that measurement is independent of the sample viscosity, which may vary from sample to sample. Observing the endpoint of a reaction allowed to run to completion also provides a maximal signal and therefore a better signal to noise ratio.

After incubation, kit 10 is placed in fluorimeter 59, stopper 16 cooperating with aperture plate 65 to position end face 24 of fiber 12 in the appropriate location relative to the fluorimeter's optical train. Radiation of a wavelength chosen to excite fluorescence in fluorophores 52 is supplied by light source 60, via dichroic beam splitter 62 and objective 64, so as to illuminate end face 24 of fiber 12 within the cone angle defined by the numerical aperture of the fiber. This radiation is consequently propagated within fiber 12 at or above the critical angle (as indicated by ray 54 in FIG. 3), and multiply totally internally reflecting along the length of the fiber. As a result, an evanescent wave is produced in fluid 43 adjacent the fiber. Competitive binding of tagged components 50 and untagged components 54 to moieties 46 attached to the fiber results in fluroescently tagged complexes 46C in proportion to the relative concentration of tagged to untagged components. Excited by the evanescent wave, the tagged complexes 46C fluoresce. A portion of the fluorescent emission tunnels into the fiber, propagating within the fiber along paths exceeding the critical angle, as indicated, for instance, by ray 56 in FIG. 3. One-half or more of this totally reflected fluorescence emission exits the fiber at end face 24, where it is collected by objective 64 and projected toward photodetector 66. As fluorescence occurs at longer wavelengths (lower frequencies) than the exciting radiation, the low-pass dichroic beam splitter 62 allows this radiation to pass to the photodetector, which in turn provides an electrical signal proportional to the intensity of the fluoescence. Dichroic beam splitter 62 also allows some radiation from source 60 to illuminate reference detector 68, which provides an electrical signal proportional to the source intensity. These two electrical signals are ratioed by ratio amplifier 70, to provide an electrical output signal proportional to fluorescent intensity corrected for source intensity variations, which is displayed by display 72.

It will be appreciated that the present invention is not limited to the apparatus so far described nor to the experimental protocols outlined hereinabove. Thus, while the sample within tube 14 will be retained by capillarity as soon as the tube is withdrawn from the sample, evaporation at the sample's free surface will eventually reduce the sample within the tube. Accordingly, it may be advantageous to seal the tube with a nonfluorescent mastic as soon as the sample is collected. Alternatively, the sample may be protected from rapid evaporation by putting a terminal constriction, as generally indicated by index numeral 90 of kit 110 (FIG. 2) in capillary tube 114. Constriction 90 is limited to the region opposite the lower inert region 32 of fiber 12, and is typically given a minimum inside diameter some 100 microns greater than the diameter of the fiber (i.e., for the 200 micron fiber of the preferred embodiment, the minimum inside diameter of constriction 60 is some 300 microns). In all other respects, kit 110 may be similar to kit 10.

It will also be recognized that any needed buffering reagent could be in the form of a lyophilized powder packed inside the capillary (for such an embodiment, the structure of capillary tube 114 recommends itself). However, given the large surface to volume ratio of kit 10, the buffer might also be coated on the the fiber or the inside wall of capillary tube 14 in the form of amphoteric polyelectrolytes (which could be proteins). In particular, such material might be coated on the inside capillary wall as a reagent coating 130 (illustrated in FIG. 2). As the wall of capillary tube 14 has a larger area than the free area of fiber 12, it is well suited for coatings of reagent required in addition to that incorporated in activated region 30, particularly if considerable additional reagent is required. It will also be appreciated that other reagents, such as anticoagulants, might be coated on the fiber or capillary tube.

Figure 2:
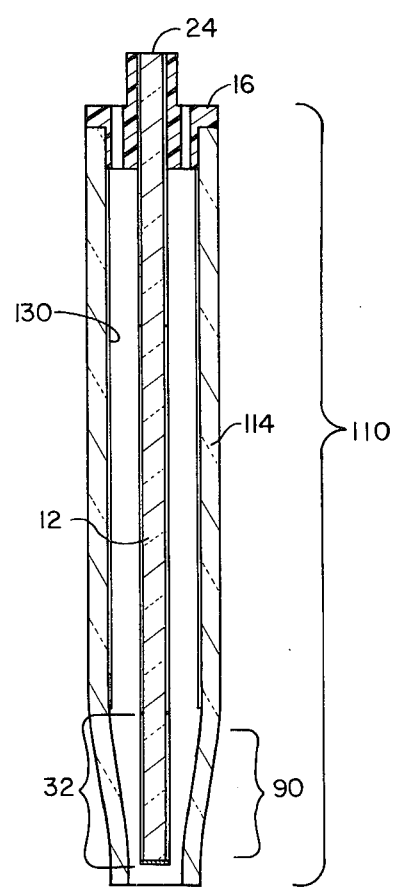
FIG. 2 is a view, similar to FIG. 1, of an alternative embodiment of the immunoassay kit of the present invention.

It might be noted further that the fiber diameter must not only be constant along its length, but must also be constant from disposable to disposable. Otherwise, while the overall amount of sample would be constant from test to test, the amount of reagent would vary. This accuracy requirement could be avoided by coating the tagged antigen on the inside wall of the capillary as reagent coating 130 (FIG. 2). This would not only reduce the diameter constancy requirement on the fiber but also on the capillary, since a diameter increase of the latter would increase not only the reagent amount but also that of the sample, while for the fiber, a resulting increase in the number of binding sites would be compensated by the reduction in the number of reflections (provided the illumination throughput was matched to the minimal fiber diameter).

It will also be understood that fiber 12 and tube 14 might be of other than right circular cylindrical shape, and that, for instance, they might be a pair of parallel plates with a capillary spacing therebetween.

It will further be appreciated that while the use of the apparatus has been described as not requiring the removal of fiber 12 from capillary tube 14, such disassembly of kit 10 may be performed in order to accommodate alternative protocols as, for instance, a wash or dilution step or a reagent exposure following sample exposure. Thus, for instance, in performing sandwich-type assays, after binding a multivalent antigen to the immobilized antibody of activated region 30, fiber 12 must be exposed to tagged antibody, generally following a wash or a dilution step. While the required changes of fluid might be accomplished by aspiration, it might prove more convenient to manipulate fiber 12 between capillary tubes or other fluid enclosures.

Since these and certain other changes may be made in the above apparatus and method without departing from the scope of the invention herein involved, it is intended that all matter contained in the above description or shown in the accompanying drawing shall be interpreted in an illustrative and not a limiting sense.

What is claimed is:

1. Apparatus for performing immunoassays using an antigen-antibody complex incorporating a fluorescent tag capable of emitting fluorescent radiation when excited by exciting radiation, said apparatus comprising in combination:
    an optical fiber transmissive to both said exciting radiation and said fluorescent radiation;
    a coating on at least a portion of said fiber, said coating having a plurality of sites, each being capable of having attached thereto a selected moiety of said antigen-antibody complex so as to leave substantially unaffected the activity of said selected moiety for forming said antigen-antibody complex; and
    means for controlling a volume of capillary dimensions bounded by said portion of said fiber.

2. Apparatus according to claim 1 wherein said coating is on a predetermined length of said fiber.

3. Apparatus according to claim 1 wherein a plurality of selected moieties of said antigen-antibody complex are attached to said coating.

4. Apparatus according to claim 3 wherein said selected moieties are attached to substantially all of said plurality of sites.

5. Apparatus according to claim 3 wherein said selected moieties and a plurality of particles of an immunologically inert material are attached in a predetermined ratio to substantially all of said plurality of sites.

6. Apparatus according to claim 5 wherein a plurality of tagged complement to said moieties are complexed to said moieties.

7. Apparatus according to claim 1 wherein said capillary dimensions are predetermined.

8. Apparatus according to claim 7 wherein said means for controlling comprises an elongate enclosure means dimensioned to surround said fiber in a spaced-apart relationship of capillary dimensions and means for positioning said fiber in said relationship within said enclosure means.

9. Apparatus according to claim 8 wherein said elongate enclosure means is a capillary tube.

10. Apparatus according to claim 9 wherein at least a portion of the interior of said capillary tube is provided a reagent coating.

11. Apparatus according to claim 9 wherein said means for positioning said fiber includes a substantially centrally apertured stopper mounted in a first end of said capillary tube, said fiber being positioned in said aperture.

12. Apparatus according to claim 11 wherein said stopper is provided with locating means for defining the location of an end of said fiber.

13. Apparatus according to claim 11 wherein the opposite end of said capillary tube is dimensioned to have a smaller inside diameter than the remainder of said capillary tube.

14. Apparatus for performing immunoassays wherein a fluorescent tag capable of emitting fluorescent radiation when excited by more energetic exciting radiation is incorporated in a constituent of an antigen-antibody complex, said apparatus comprising in combination:
    an optical fiber transmissive to both said exciting radiation and said fluorescent radiation, a predetermined length of said fiber having immobilized thereto a selected moiety of a desired antigen-antibody complex in a predetermined surface concentration;
    a capillary tube dimensioned to accept said fiber in spaced-apart relationship; and
    a stopper affixed to a first end of said capillary tube, said stopper supporting said fiber substantially coaxially within said capillary tube with said fiber passing through said stopper substantially centrally, said stopper having a locating means for defining the location of an end of said fiber.

15. A method for immunoassay employing an optical element transmissive to excitation radiation which can excite fluorescence of a fluorescent tag included as a constituent of an antigen-antibody complex, said element being also transmissive to said fluorescence, said optical element having selected moieties of said antibody-antigen complex attached to a pre-determined area of its surface, said method comprising the steps of:
    immersing said optical element in a fluid sample to be assayed so that the portion of said sample immunologically reactive with said selected moieties can react therewith to form said complex;
    controlling the immersion of said optical element in said fluid sample so as to insure that said predetermined area is completely covered with a layer of known thickness of said fluid sample;
    incubating said optical element in said layer of fluid sample for a time in excess of the time required for diffusional processes to scavenge the volume of sample defined by said known area and said known thickness;
    illuminating said optical element with an evanescent electromagnetic wave of said excitation radiation so as to excite fluorescence of said tag in said complex attached to said optical element; and
    measuring the intensity of said fluorescence.

* * * * *